(12) United States Patent
Hartman (10) Patent No.: US 6,413,268 B1
(45) Date of Patent: Jul. 2, 2002

(54) APPARATUS AND METHOD FOR TARGETED UV PHOTOTHERAPY OF SKIN DISORDERS

(76) Inventor: Raymond A. Hartman, 3003 Azahar St., Carlsbad, CA (US) 92009

(*) Notice: Subject to any disclaimer, the term of this patent is extended or adjusted under 35 U.S.C. 154(b) by 130 days.

(21) Appl. No.: 09/637,343

(22) Filed: Aug. 11, 2000

(51) Int. Cl.[7] .................................................. A61N 5/06
(52) U.S. Cl. .............................. 607/94; 607/88; 606/9; 606/17; 250/504
(58) Field of Search .............................. 607/94, 88–95; 606/9–20

(56) References Cited

U.S. PATENT DOCUMENTS

| | | | |
|---|---|---|---|
| 1,800,277 A | | 4/1931 | Boerstler |
| 4,149,086 A | | 4/1979 | Nath |
| 4,155,025 A | | 5/1979 | Dobrusskin et al. |
| 4,177,384 A | | 12/1979 | Wolff |
| 4,287,554 A | | 9/1981 | Wolff |
| 4,298,806 A | | 11/1981 | Herold |
| 4,385,344 A | * | 5/1983 | Gonser .................... 250/503.1 |
| 4,444,190 A | | 4/1984 | Mutzhas |
| 4,558,700 A | | 12/1985 | Mutzhas |
| 4,560,883 A | * | 12/1985 | Kerschgens .............. 250/493.1 |
| 4,686,986 A | * | 8/1987 | Fenyo et al. .................. 607/90 |

(List continued on next page.)

FOREIGN PATENT DOCUMENTS

| | | |
|---|---|---|
| DE | 76 13 630 | 11/1976 |
| DE | 41 12275 | 11/1992 |

OTHER PUBLICATIONS

Parrish et al., Action Spectrum for Phototherapy of Psoriasis, The Journal of Investigative Dermatology, 1981, pp. 359–362, vol. 76, No. 5.
Laser Photonics Press Release, Feb. 2000, Yahoo! Finance.
Surgilight Laser Technology brochure, last update Apr. 10, 2000.

Primary Examiner—Lee Cohen
Assistant Examiner—H. M. Johnson
(74) Attorney, Agent, or Firm—Brown, Martin, Haller & McClain, LLP (57) ABSTRACT

A UV phototherapy apparatus has a base unit containing a UVB arc lamp and an output port for delivery of UVB radiation within a predetermined range. A flexible, elongate optical guide is connected to the output port at one end and to a handpiece at the opposite end. The handpiece is arranged to convert the round beam from the optical guide into a predetermined straight-edged shape such as a rectangular beam, and has an exit aperture of corresponding shape for delivering the shaped beam to a target area of a patient. A beam isolating assembly in the optical path isolates UVB radiation in the predetermined range from the lamp output, so that at least 90% of the radiation directed into the optical guide is in the predetermined range.

32 Claims, 3 Drawing Sheets

U.S. PATENT DOCUMENTS

| | | |
|---|---|---|
| 4,860,172 A | 8/1989 | Schlager |
| 4,909,254 A | 3/1990 | Wilkinson |
| 4,939,374 A | 7/1990 | Greutert |
| 4,950,903 A | 8/1990 | Frankena |
| 4,959,551 A | 9/1990 | Schlitt |
| 5,205,291 A | 4/1993 | Potter |
| 5,216,539 A | 6/1993 | Boher et al. |
| 5,300,097 A | 4/1994 | Lerner et al. |
| 5,320,618 A | 6/1994 | Gustafsson |
| 5,337,741 A | 8/1994 | Diamond |
| 5,344,434 A | 9/1994 | Talmore |
| 5,426,308 A | 6/1995 | Sudduth et al. |
| 5,433,988 A | 7/1995 | Fukuda et al. |
| 5,441,531 A | 8/1995 | Zarate et al. |
| 5,511,563 A | 4/1996 | Diamond |
| 5,540,978 A | 7/1996 | Schrenk |
| 5,563,420 A | 10/1996 | Sullivan et al. |
| 5,569,977 A | 10/1996 | Donofrio |
| 5,608,227 A | 3/1997 | Dierks et al. |
| 5,612,001 A | 3/1997 | Matschke |
| 5,628,744 A | 5/1997 | Coleman et al. |
| 5,658,275 A * | 8/1997 | Saadat ............ 606/15 |
| 5,720,772 A | 2/1998 | Eckhouse |
| 5,769,844 A | 6/1998 | Ghaffari |
| 5,782,895 A | 7/1998 | Zarate et al. |
| 5,836,999 A | 11/1998 | Eckhouse et al. |
| 5,843,143 A * | 12/1998 | Whitehurst ............ 607/88 |
| 5,849,027 A | 12/1998 | Gart et al. |
| 5,874,741 A | 2/1999 | Matschke |
| 5,879,159 A | 3/1999 | Cipolla |
| 5,908,415 A | 6/1999 | Sinofsky |
| 5,925,034 A | 7/1999 | Buckley et al. |
| 5,934,780 A | 8/1999 | Tanaka |
| 5,961,543 A | 10/1999 | Waldmann |
| 5,989,283 A | 11/1999 | Wilkens |
| 6,223,071 B1 | 4/2001 | Lundahl et al. |

* cited by examiner

FIG. 7

APPARATUS AND METHOD FOR TARGETED UV PHOTOTHERAPY OF SKIN DISORDERS

BACKGROUND OF THE INVENTION

The present invention relates generally to a UV phototherapy apparatus and method for treatment of dermatoses or skin disorders such as psoriasis, vitiligo, eczema, rosacea, alopecia, and the like, and is particularly concerned with a targeted UV phototherapy apparatus and method in which radiation is applied to successive specific areas of a lesion.

Phototherapy is the use of ultraviolet radiation to achieve therapeutic benefit to dermatoses (psoriasis, vitiligo, rosacea, alopecia, eczema). The UV spectrum is divided into UVA (320–400 nm), UVB (290–320 nm) and UVC (100–290 nm). The UVA region is considered the longwave UV spectrum responsible for tanning effects, the UVB region is considered the sunburning region (erythemal region), and UVC is considered the germicidal region. Typically, both UVA and UVB radiation have been used for treatment of dermatoses. Treatment with UVA radiation is called photochemical therapy and involves the use of a photosensitizing agent, psoralen, and the administration of UVA radiation. The basis for phototherapy is believed to be the direct interaction of light of certain frequencies with tissue to cause a change in immune response. U.S. Pat. No. 5,696,081 of Ulirich describes the immune response caused by UVA and UVB radiation.

Phototherapy has a long history of treating psoriasis dating back to 1926 when natural solar treatments such as the Goekerman regimen and Heliotherapy (sunlight rich in UVB at the Dead Sea) were practiced. Heliotherapy is still practiced today. However, these natural solar treatments have mostly given way to modern booths or chambers that provide artificial UVA and/or UVB radiation. Although the benefits of UVA and UVB are known in dermatoses treatment, the adverse affects upon healthy tissue, particularly of UVB radiation, are also well known and a medical concern.

Most of the devices designed for phototherapy, both in the UVA and UVB, are table top projectors for irradiating the face or feet, or booth or chamber types of devices (solaria). Various UV booth apparatuses are revealed in U.S. Pat. Nos. 4,095,113, 4,103,175, 4,100,415, 4,703,184, 4,177,384, 4,959,551, 4,469,951 and 4,309,616. All of these devices rely upon tubular fluorescent or tubular mercury bulbs as UV sources. The booths are generally composed of multiple banks of bulbs, and irradiate large areas, usually the whole body. Large unaffected portions of the body can be protected with draping or wrapping materials, but this is impractical for most clinical use. The large area (whole body or limb) radiation pattern of these devices is a result of the emission characteristics of the light sources. The diffuse, lambertian emission patterns from these elongated, cylindrical bulbs are difficult to aim or direct to specific areas. To achieve sufficient radiation levels to provide therapeutic affect, large numbers of bulbs are required to achieve treatment times within practical limits. It is common for a booth to have 24 to 48 bulbs to achieve these practical fluence levels.

Generally, the dose of UVB radiation administered in a booth is limited by erythemal (sunburning) action. The absolute amount of UVB that a given person can tolerate before burning varies by skin type and prior exposure. It also varies with the composition of the UVB, because shorter wavelengths have greater erythemal activity. Normally, before treatment is given, the minimum erythemal dose (MED) for each patient is determined by applying different radiation doses in small patches to healthy tissue. These patches indicate the amount of energy (usually expressed in $mj/cm^2$) that will result in sunburning the patient. It is typical for the patches to be viewed at 24 hours, and the patch that is slightly pink is considered the MED level. A single booth treatment starts at some percentage (often 70%) of this MED, and then may be increased in follow up sessions as tolerance builds up due to tanning. A typical cycle of treatments for therapeutic success in a booth is 15 to 30 treatments, usually administered in 2 to 3 treatments per week. The amount of radiation given in a given session is limited by the radiation exposure of the healthy tissue. Sunburning the entire body is not only painful, but also medically unwise.

A similar technique is used for UVA treatment, but the dose is called the MPD and the reading is generally 72 hours after exposure. In both cases, however, the MED or MPD is determined by radiation on healthy (non-lesional) tissue.

Much of the UVA therapy has been replaced by PUVA therapy, called photochemical therapy, where the photosensitizer psoralen or one of its derivatives used with UVA radiation. PUVA treatment has proven to have long term oncological manifestations not seen with UVB treatment. However, when UVB treatment has not been successful, the alternative of PUVA does provide relief, albeit at a potential health risk.

It has been demonstrated that some lesional tissue (psoriatic plaque for example) can withstand much more UVB radiation than healthy tissue. This is largely due to the thickness of the plaque areas. However, the radiation delivered to the plaque in booth therapy is limited to the amount of radiation that the adjacent health tissue can withstand. There are three negative aspects of booth UVB treatment. First, the radiation is provided to both healthy and lesional tissue, thus increasing the total body UVB exposure. It has been demonstrated that this cumulative total body exposure has carcinogenic implications. Second, the low radiation threshold of healthy tissue limits the amount of radiation that may be delivered per session to the lesional areas. This sub-optimal dosage results in an increased number of treatments to achieve the cumulative lesional radiation required for therapeutic success. Third, the increased number of treatments that result from low plaque doses again increases the total body radiation received.

The article entitled "Action Spectrum for Phototherapy of Psoriasis", by John A. Parrish, M.D. and Kurt F. Jaenicke, B.A., published in the Journal of Investigative Dermatology, Vol. 76, No. 5, p. 359–362 (1981) describes the psoriasis action spectrum from 253 nm to 313 nm. The results in this article indicate that radiation below 296 nm is highly erythemal but not therapeutic. The article also reports that the level of radiation to deliver 1 MED at 300 nm is about 1/10 the radiation level required to achieve 1 MED at 313 nm. This confirms the higher erythemal activity of shorter wavelength UVB. Conventional UVB fluorescent sources provide UV radiation from 275–340 nm, a result of the fluorescent material bandwidth, and hence provide significant radiation of erythemal activity without therapeutic affect. Since a high proportion of this conventional flourescent radiation is non-therapeutic, but erythemally limiting, it necessitates a larger number of treatments.

The presence of the erythemally limiting but non-therapeutic radiation from conventional sources has led to the development of more effective UVB lamps for phototherapy. Sources of monochromatic radiation at 308 nm are available in the form of excimer lamps (U.S. Pat. No. 5,955,840). Also, tubular fluorescent lamps nearly monochromatic output at 311 nm (U.S. Pat. No. 4,354,139) are available. Both these lamp sources suffer from the disadvantages of large area radiation, i.e. erythemal limits per treatment and healthy tissue radiation. However, many reports are available on the advantages of monochromatic UVB from these lamps. One advantage is the lack of non-therapeutic, erythemal radiation below 296 nm. This allows more of the delivered UVB radiation to be of therapeutic value before the MED is reached. Conventional UVB bulbs which operate in the broad range of 275–340 nm may provide undesirable radiation which promotes cellular proliferation.

As opposed to this large area radiation, targeted phototherapy is the application of radiation to specific areas, defined by the geometry or exit aperture of a delivery device. The radiation dose is generally, although not necessarily, constant through out the application to a lesion. The dose administered during an irradiation cycle is known, and the boundary of the irradiated area is known. It may be thought of as placing a penlight against the skin. The area is known to be the exit area of the penlight, and, in the case of targeted phototherapy, the dose may be controlled. Repeating this pattern of the penlight exit face over a lesion allows for complete coverage of the lesion. Tubular fluorescent lamps in general cannot be effectively used for targeted radiation delivery. This is due to the difficulty in collecting the light from these elongated, diffuse sources, and focusing it onto the skin or into an optical guide. Targeted, or spot delivery of radiation in general requires that the light source be collimated or be of a small intense arc that allows efficient fiber optic coupling. Targeted UV phototherapy systems typically employ lasers and are very expensive.

Monochromatic radiation at 308 nm can be provided by xenon chloride excimer lasers, and such sources are capable of directed site delivery as a result of their coherent beams. The disadvantage of such sources is the high cost of equipment and associated maintenance. They nominally sell in the hundreds of thousands of dollars, and contain high-pressure toxic gases that must be regularly exchanged.

SUMMARY OF THE INVENTION

It is an object of the present invention to provide a new and improved apparatus and method for targeted UV phototherapy of skin disorders.

According to one aspect of the present invention, a UV phototherapy apparatus is provided which comprises a base unit having an output port for delivery of UVB radiation within a predetermined range, an optical guide having an input end connected to the output port of the base unit and an output end, and a handpiece having an input end connected to the output end of the optical guide, and an exit aperture of predetermined, non-circular shape for delivering radiation to a target area of a patient, the base unit including a UVB lamp for emitting UVB radiation in a predetermined range, a focusing device for focusing the radiation from the UVB lamp along an optical path onto the input end of the optical guide, and a beam isolating assembly in the optical path for isolating UVB radiation from the lamp in the predetermined range from the remainder of the lamp output whereby at least 90% of the radiation directed into the optical guide is in the predetermined range:

In one example, the predetermined UVB range was between 300 nm and 320 nm. The beam isolating assembly may comprise at least one UVB reflective dichroic mirror for reflecting radiation in the range from 300 nm to 320 nm along the optical path while transmitting substantially all radiation outside the desired range. In a preferred embodiment, two UVB reflective dichroic mirrors are arranged in series along the optical path, for further reduction of unwanted radiation. In one embodiment of the invention, the base unit is provided with a first output port for UVB radiation and a second output port for UVA radiation. A first optical guide and handpiece are connected to the first output port, and a second optical guide and handpiece may be connected to the second output port. The beam isolating assembly includes a mechanism for isolating UVB radiation in a predetermined range and directing the isolated UVB radiation to the first output port, and a mechanism for isolating UVA radiation in a predetermined range and directing the isolated UVA radiation to the second output port. This provides for optional directed UVB therapy with the first handpiece or directed UVA therapy or photochemical therapy using the second output port and connected handpiece.

The UVB lamp is preferably a medium pressure, short or medium arc mercury lamp such as a mercury, xenon mercury, or doped mercury short arc lamp. This type of lamp has the highest proportion of its output in the 300 to 320 nm. UVB and has an output which can be readily and accurately directed by a focusing assembly into the input end of an optical guide of small dimensions, unlike a tubular fluorescent lamp.

The handpiece in one embodiment includes beam shaping optics for expanding the circular beam output from the optical guide into a larger, square beam. The handpiece may be a square tube with polished inner walls, in one example. The square beam output allows for successive side-by-side treatments of adjacent areas of a lesion without any overlap between treatment areas.

According to another aspect of the present invention, a method of treating lesional tissue with targeted UVB radiation is provided, which comprises directing radiation from a UVB lamp source along an optical path, isolating radiation in a predetermined UVB range from the radiation spectrum emitted by the lamp source and directing the isolated UVB radiation into one end of an optical guide,.and connecting the other end of the optical guide to a handpiece having an exit aperture of predetermined, non-circular shape for directing the isolated radiation onto a predetermined target area of tissue to be treated.

Up until now, the only effective devices for applying targeted phototherapy to specific areas of lesional tissue, without applying unwanted radiation to healthy skin in surrounding areas, used a xenon chloride excimer laser as the UVB light source. These devices are large and extremely expensive, require frequent maintenance, and use high-pressure toxic gases, such that these devices can typically only be used in a doctor's office, and cannot be used by the patient at home. The apparatus and method of this invention provides targeted UVB phototherapy using a much smaller apparatus and an inexpensive UVB lamp as the radiation source. The apparatus is much less expensive, requires less maintenance, and can conveniently be used by a patient at home.

BRIEF DESCRIPTION OF THE DRAWINGS

The present invention will be better understood from the following detailed description of some exemplary embodiments of the invention, taken in conjunction with the accompanying drawings in which like reference numerals refer to like parts and in which.

DETAILED DESCRIPTION OF THE DRAWINGS

Figure 1:
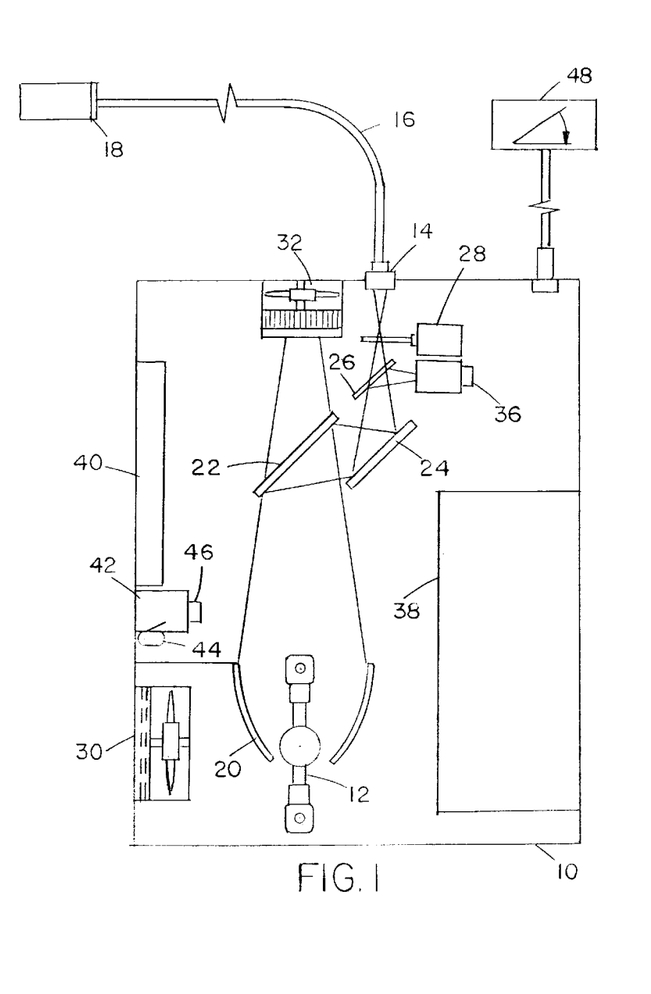
FIG. 1 is a block diagram of a targeted UVB phototherapy apparatus according to a first embodiment of the invention.

FIG. 1 illustrates a targeted UV phototherapy apparatus according to a first exemplary embodiment of the invention. The apparatus basically comprises a base unit or housing 10 containing a UVB lamp 12 and having an output port 14 for UVB radiation, an elongate light guide 16 having a first end connected to the output port 14 and a second end, and a handpiece 18 connected to the second end of the light guide 16. The handpiece is designed for targeted delivery of UVB radiation to a skin area to be treated, as discussed in more detail below with reference to FIGS. 3 and 4.

The UVB lamp 12 is specifically selected to be highly efficient and to have an output with a high proportion of UVB radiation. Preferably, the lamp is a medium pressure, short or medium arc mercury lamp such as a mercury, doped mercury, or xenon mercury lamp. An optical assembly within the housing or base unit 10 directs radiation in a predetermined UVB range from lamp 12 to output port 14. The optical assembly includes a symmetrical reflector 20 enclosing the lamp, and a series of two UVB reflective mirrors 22,24 in the optical path for directing radiation in the predetermined range towards the output port. An edge filter 26 and a shutter 28 are located in the optical path from the second mirror 24 to the output port 14.

The UV reflector may be of metal or dichroic coated glass that is UV reflective. This can eliminate as much as 75% of the unwanted radiation from the reflected light. Cooling air is ducted from a filtered fan 30 onto the reflector to avoid heat distortion. The UV reflector is arranged to focus the collected radiation onto output port 14, as illustrated in FIG. 1. The reflector 20 directs the collected radiation from lamp 12 to the first UVB reflective dichroic mirror 22, which is arranged at an angle of 45° to the light path. This mirror reflects 95% of the received UVB radiation to the second UVB reflective dichroic mirror 24, while the majority of the unwanted radiation outside the predetermined UVB range is transmitted through mirror 22 and collected by a fan and heat sink assembly 32 which is coated with a black body absorbent material. The second mirror also reflects 95% of the desired UVB radiation to edge filter 26. The two mirrors reflect at 95% in the region of 280 nm to 325 nm. Since mercury lamps do not have any significant output from 320 to 325 nm., the radiation reflected from the second mirror will be predominately in the range from 280 nm to 320 nm. The edge filter 26 eliminates or attenuates radiation below 300 nm., such as residual 254 nm. radiation and the mercury 296 nm. line, producing an output beam that is predominantly (at least 90%) composed of radiation within the range from 300 nm. to 320 nm. The edge filter preferably comprises a beam splitter which directs a small amount of the radiation onto a continuous energy monitor or sensor 36. The beam splitter may be made of a Schott WG 295 material to reduce the 296 nm line of the mercury lamp spectrum.

The mirror arrangement ensures that only about 10% of the radiation within the desired UVB range is lost, unlike band pass filters which are very inefficient. About 5% of the unwanted radiation outside the range will be reflected by each mirror and included in the UVB beam, but by using two mirrors this unwanted radiation is reduced to 0.25%. Suitable UVB dichroic mirrors are available from Oriel Instruments of Stratford, Connecticut, and other optical suppliers.

In the case of a short arc mercury lamp, the beam transmitted from the lamp is not continuous, but consists mainly of peaks at 300 nm., 302 nm, and 313 nm. Optional dopant peaks at 307 nm. and 318 nm. can be provided by suitable lamp selection. The actual mix of wavelengths within the range will be dependent on the peaks of the actual mercury lamp selected. Thus, for a mercury xenon lamp, the output will be 90% between 302 and 313 nm. The mercury xenon lamp may be doped with an additive that has a 318 nm. radiation peak, allowing the range to be extended if desired. Thus, although the range is stated to be from 300 nm. to 320 nm., the radiation will actual be a mixture of various specific wavelengths within this range, dependent on the specific type of lamp selected. As noted above, a mercury xenon source will have strong lines at 302 nm. and 313 nm. A mixture of radiation in these two wavelengths will have the added plaque penetration power of the longer wavelength UVB radiation, and the faster clearing rate of the shorter wavelength UVB radiation. A mix of UVB wavelengths, rather than monochromatic UVB, will have greater therapeutic value. The size of the lamp may be between 500–1200 watts, which will deliver between 2.0 to 4.8 watts from the handpiece.

The beam shutter 28 placed in the light path between the edge filter 26 and output port acts to control the output of UVB radiation from the base unit into the light guide and handpiece. The shutter construction allows for sufficient area and cooling to dissipate an average energy of 2–4 watts. Alternatively, it maybe arranged to reflect the beam into a suitably positioned heat sink, when extended into the closed position. When open, the shutter provides a clear path for the reflected beam into the light guide 16.

The lamp 12 is connected to a suitable power supply and ignition unit 38 within the housing or base unit. Alternatively, the unit 38 may be provided in a separate enclosure with appropriate control and output connections to the base unit. A control unit 40 for monitoring and controlling lamp operation is also mounted in the housing 10. The control unit is connected to the shutter 28 and the output of sensor 36, as well as to the lamp power supply and ignition unit 38. It is associated with a control panel (not illustrated) on the outside of housing 10 for user control inputs and monitoring. A calibration port 42 is provided for handpiece 18. Calibration port 42 has a switch 44 in its side wall for detecting insertion of the handpiece, and a sensor 46 at its inner end for monitoring the output of the handpiece. The output of sensor 46 is also connected to control unit 40. A switch such as foot switch 48 may be provided for switching the apparatus on and off, although a manually operated on/off switch may alternatively be provided on the control panel.

The light guide 16 is either a liquid light guide or a quartz or fused silica fiberoptic guide. The numerical aperture (NA) of the light guide must define an input acceptance angle which equals or exceeds the focusing angle or conical angle of the reflector for maximum coupling. Flexible fluid filled light guides with input faces up to 8 mm. in diameter are available which have numerical apertures as high as 0.55, and afford easy direct coupling to the output port 14. Smaller diameter fiberoptic guides can be coupled with the use of fused silica lenses.

The distal end of light guide 16 is coupled to handpiece 18, which is designed for directed, targeted application of the UVB radiation to a lesion area. A handpiece 18 is illustrated in more detail in FIGS. 3 and 4. The handpiece basically comprises a tube 50 of square cross section having a base 52 at one end with an input port for receiving the exit end 54 of the light guide, an internal chamber 55, and an open exit end in which a fused silica rod 56 of square cross-section is cemented. The cement has an index of refraction lower than that of fused silica, and acts as a liquid seal to prevent entry of contaminants into the handpiece chamber. The end of the light guide 16 is secured in the input port of the tube 50 by a suitable connector 53.

Figure 3:
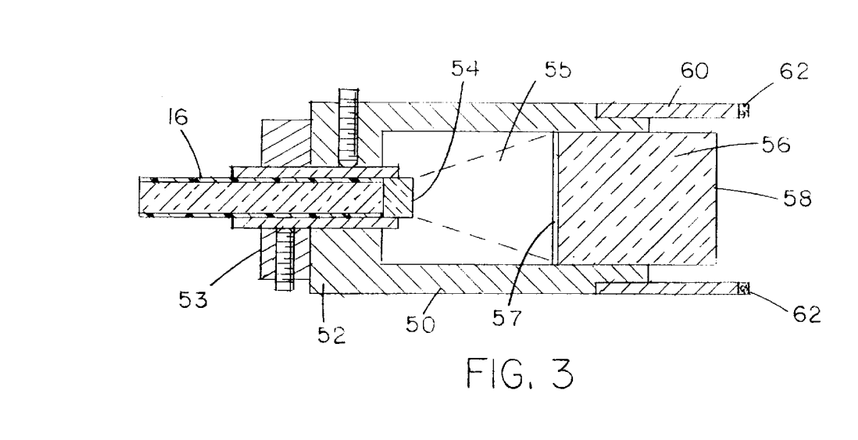
FIG. 3 is a cross sectional view of a handpiece for use in the apparatus of FIG. 1 or 2.
Figure 4:
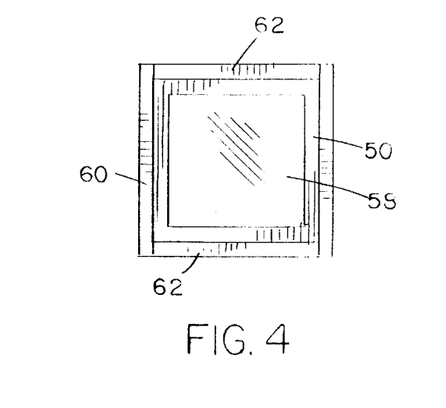
FIG. 4 is a front end elevational view of the handpiece of FIG. 3.

The entrance face 57 of rod 55 is roughened to provide increased diffusion of incoming radiation. The exit face 58 of the rod defines an exit aperture for UVB radiation. The tube 50 is of a material which is opaque to UVB radiation to prevent escape of radiation from the tube other than via the exit aperture 58. Suitable materials are aluminum and UV blocking plastic or glass materials. The material may be selected to be transmissive in the visible region, for better visualization of the area to be irradiated. This can be accomplished by various plastics such as polycarbonate, as well as UV blocking glass materials. The inside walls of chamber 55 are preferably polished in order to re-direct scattered radiation onto the entrance face 57 of rod 56. A disposable slide-on tip or shield 60 of clear, UV blocking plastic material is mounted to project from the open end of tube 50 and beyond the exit face 58 of the rod 56. This tip is designed to be placed against the skin during treatment, so as to block UV radiation from exiting into the room. Since it is of clear or transparent plastic, the lesion area will still be visible during treatment. Ink or dye-containing felt or porous pads 62 may be mounted at the end of tip 60 in order to mark skin areas as they are treated. The pads 62 will mark the top and bottom edge of a square area which has been treated. Alternatively, a pad of square section may encompass the entire area irradiated, or other arrangements may be provided in order to mark the area.

In an alternative arrangement, the marking pads 62 may be eliminated, and the lesion or skin area to be treated may instead be covered or striped with a dilute aqueous solution of a photobleachable or photolabile dye. Such dyes lose color or intensity when exposed to UV light. Photochromic dyes which change color on exposure to UV are also readily available, and may be used for this purpose. By keeping the concentration of dye low, and by the use of thin stripes made by a roller or stamp, the amount of UV absorbed by the dye maybe kept to a minimum. The dispersion qualities of the plaque will ensure complete coverage of the applied radiation.

The exit aperture geometry of the handpiece establishes the shape and area which is irradiated at any time. The handpiece is optically designed to expand and shape the output beam from the light guide from a circular beam into a larger, square beam. By making the exit beam of square or rectangular shape, an area to be irradiated can be completely covered by repeated application of the handpiece to adjacent areas, without any overlap with previously treated areas. For this purpose, the exit aperture must have straight, not curved, edges. Another suitable shape for the exit aperture would be an equilateral triangle. The interior of the handpiece is designed to expand and homogenize the beam from a small, round cross-section beam exiting the light guide, into a larger, square cross-section output from exit aperture 58. Beam shaping is accomplished by the square, fused silica rod 56, which will project a square beam. If desired, a diffuser plate may be added to reduce non-homogeneous output, and a mirror can be used if a right angle bend is required in the handpiece for convenience of application.

Operation of the apparatus of FIGS. 1, 3 and 4 will now be described in more detail. The exit aperture 58 of the handpiece will determine the area. of radiation which can be applied in a single does. In one example, the exit aperture 58 was a square with a length of 2 cm. on each side. The lesion is covered in a checkerboard pattern with the handpiece being applied to each 4 $cm^2$ area for a predetermined time period, dependent upon the desired dose.

Initially, the MED (minimal erythemal dose) for each patient is determined by irradiating a series of small patches of healthy skin ranging in dosage from, say, 40 $mj/cm^2$ to 120 $mj/cm^2$. The patches indicate the amount of energy which will result in sunburning the patient. The patch which is slightly pink is considered to be the MED level. Once the MED dose is determined for a patient, the physician will select a multiple of this dose for lesion application. The nominal range will be 0.7–6.0 MEDs, depending upon patch thickness and other factors known to the physician, such as the patient's response to prior phototherapy, and the location of the lesion. The regions of healthy skin surrounding the lesion will be protected with a coating of zinc oxide or a UV absorbing oil, prior to starting a treatment.

The control panel on the housing will allow the practitioner to select the desired energy density for a single dose. If the selected irradiation dose is 500 $mj/cm^2$, the irradiation cycle for each dose will be about 1 second. A microprocessor in the control unit is programmed to open the shutter 28 for this time period, after it is determined that the lamp has warmed up, and to close the shutter again at the end of a cycle, providing an audible or visible indication to the user that the cycle for one irradiated area is complete. When the apparatus is initially switched on, and as the lamp is warming up, the output of sensor 36 will be monitored. The shutter 26 is closed during the warm-up period. When the output is detected to be stable, the operator is prompted to calibrate the handpiece. The handpiece is then inserted in calibration port 42, and the foot switch 48 or a switch on the handpiece is depressed. When the switch is actuated, the shutter 26 is opened and light will enter the handpiece and be measured by the energy sensor 46 in the calibration port. Software diagnostics measure the stability of the output. If the energy sensor 46 does not detect any radiation, the shutter 26 will close and the operator will be alerted to a potential problem requiring maintenance.

On completion of the calibration, assuming that the energy sensor detects the correct output from the handpiece, an irradiation cycle can be commenced. The operator places the exit aperture end of the handpiece against a first area of the lesion, and initiates irradiation by depressing the foot switch or actuating a switch on the handpiece. This again opens the shutter for a predetermined time period controlled by the selected energy dose. The precise duration of the cycle is determined by the microprocessor, the calibration data, and the dose selection made by the practitioner. At the end of the first cycle, the operator moves the handpiece to cover an adjacent area of the lesion, and repeats the procedure, continuing to cover the lesion in a checkerboard pattern until the entire lesion area has been covered, with each treated area being marked by the ink pads or the like to ensure that the same area is not treated more than once in any treatment. The handpiece may be dipped in a sterilizing solution between uses. The slide-on tip is preferably disposable so that a new uncontaminated tip is used with each treatment.

A typical skin lesion may have an area of the order of about 100 cm$^2$. Using this apparatus, the entire lesion area can be treated in less than 3 minutes. If the exit aperture of the handpiece has an area of 4 cm$^2$, the lesion area can be covered in approximately 25 individual doses, and if each dose is around 1 second, the overall time required will be less than 2 minutes, assuming that it takes about 30 seconds to coat the adjacent, healthy skin with protective oil and about 2 seconds to move the handpiece between successive "checkerboard" doses.

The handpiece provides a stable, maneuverable means for radiation delivery, and ensures accurate, targeted radiation delivery to the area covered by the exit aperture only. This avoids irradiation of healthy tissue, allowing a higher dose to be delivered in one treatment than in a phototherapy booth, since lesional tissue is known to withstand much more UVB radiation than healthy tissue. Thus, the total number of treatments required is likely to be much less than with phototherapy booth treatment. Previously, targeted UVB radiation delivery was only possible with the use of xenon chloride excimer lasers as the UVB source, which are capable of directed site delivery due to their coherent beams. However, lasers are extremely expensive, result in large and cumbersome equipment, and require frequent and expensive maintenance. This invention provides an inexpensive, low maintenance lamp as the UV radiation source, together with an optical assembly for substantially excluding radiation outside the UVB range, and directing around 90% of the UVB radiation emitted from the lamp to the input end of the light guide.

Figure 2:
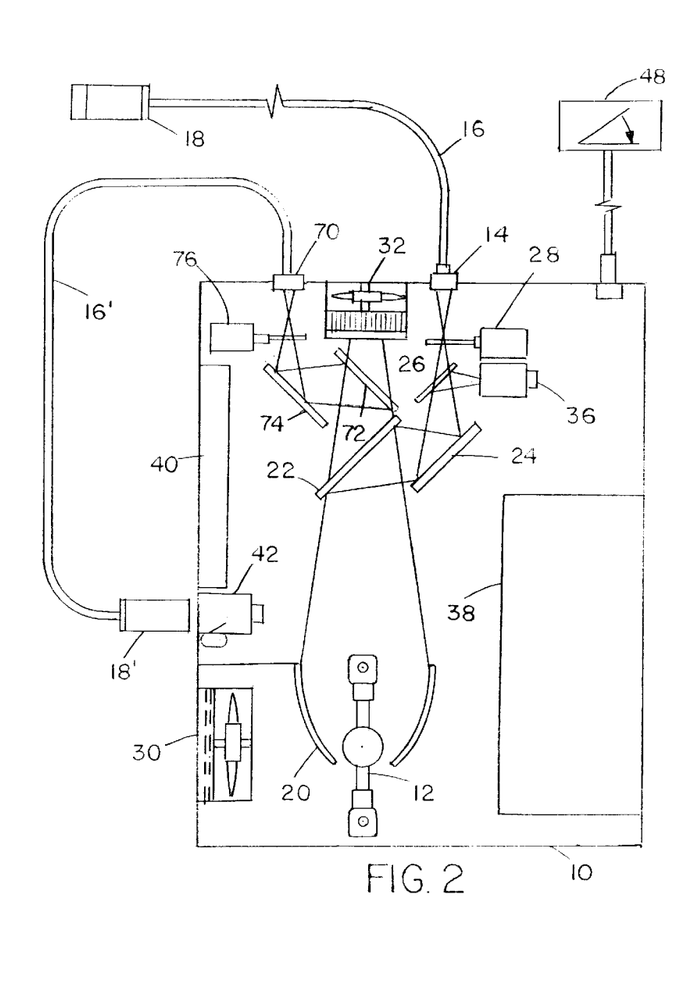
FIG. 2 is a block diagram illustrating an apparatus according to a second embodiment of the invention for selective, targeted UVB or UVA phototherapy.

FIG. 2 illustrates a targeted phototherapy apparatus according to a second exemplary embodiment of the invention, which also has the option of delivering targeted UVA radiation to a patient if desired. The apparatus is similar to that of FIG. 1, and like reference numerals have been provided for like parts as appropriate. However, in this apparatus, the housing 10 has a second output port 70 for UVA radiation, in addition to the first, UVB outlet port 14. An optical assembly is provided for directing UVA radiation emitted from lamp 12 to the second outlet port 70. This assembly basically comprises a first UVA reflective mirror 72 positioned to receive radiation transmitted by the first UVB mirror 22, and a second UVA reflective mirror 74 for receiving radiation reflected from mirror 72 and reflecting the UVA radiation onto outlet port 70. A shutter 76 is provided in the path from the second mirror 74 to the outlet port 70 for controlling output of UVA radiation from port 70, in a similar manner to shutter 28 for the UVB port.

A second optical guide 16' is connected to the outlet port 70 and a handpiece 18' identical to handpiece 18 is connected to the distal end of guide 16' for directing UVA radiation onto a selected area to be treated. Instead of providing two separate optical guides and handpieces, a single optical guide and handpiece may be used, and simply connected to the appropriate outlet port 14 or 70, depending on whether UVB or UVA treatment is desired.

The mirrors 72 and 74 may suitably comprise dichroic mirrors that reflect radiation in the UVA range from 330 to 380 nm. Dichroic mirrors which reflect at 98% in this wavelength range are commercially available, with cutoff wavelengths to prevent unwanted visible and infrared radiation. Approximately 85% of the UVA will be transmitted through the first UVB mirror, and after the two UVA mirrors, 80% of the original UVA mercury line of 365 nm. will be preserved. Output port 70 may be used for directed or targeted UVA phototherapy or photochemical therapy, using a similar procedure to that described above in connection with FIG. 1.

In the apparatus of FIG. 2, the operator will select UVB or UVA mode on the control panel, and connect the light guide and handpiece to the appropriate output port, if only one light guide and handpiece is provided. When the on/off switch is depressed, the shutter for the selected port will open and light will enter the handpiece and be measured by the energy sensor in the calibration port. The calibration step will ensure that the correct wavelength spectrum for either UVB or UVA radiation is detected by sensor 46, before treatment commences.

Figure 5:
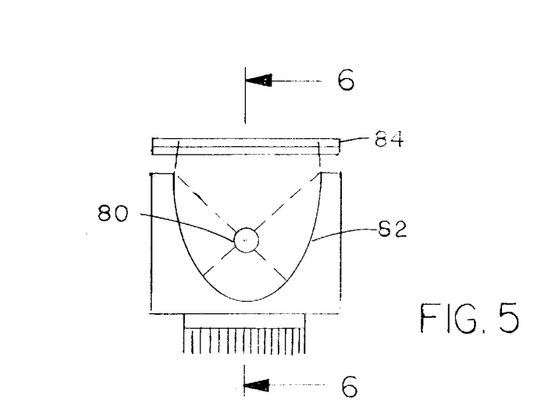
FIG. 5 is a cross-sectional view of an alternative lamp for use as the UVB source in the apparatus of FIG. 1 or FIG. 2.
Figure 6:
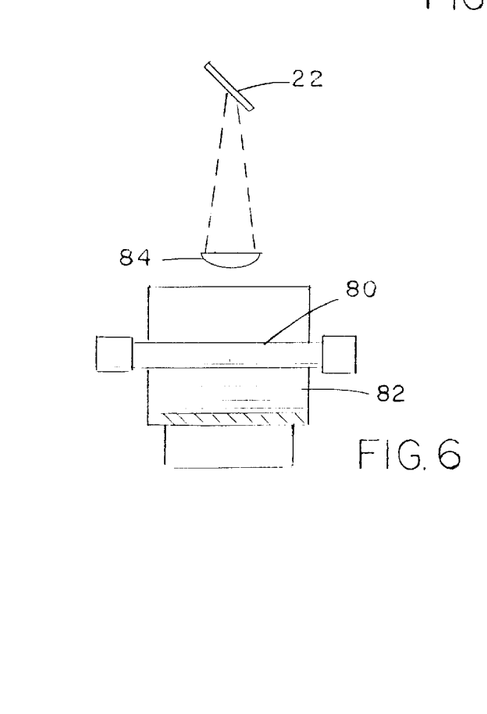
FIG. 6 is a cross-section on the lines 6—6 of FIG. 5.

In the embodiments of FIGS. 1 and 2, the lamp 12 is a mercury xenon, mercury, or doped mercury short arc lamp, and the radiation from the lamp is collected and directed towards the first mirror 22 by a symmetric elliptical or parabolic reflector 20, in order to permit coupling into the light guide. Alternatively, the lamp 12 of FIGS. 1 and 2 may be replaced by a doped metal halide or tubular mercury arc lamp 80 as illustrated in FIGS. 5 and 6. Lamp 80 has a 1–3 inch arc. This type of lamp exhibits excellent UVB production, but coupling the output into a light guide becomes more complex. Thus, in this alternative, the symmetric elliptical reflector 20 of FIGS. 1 and 2 is replaced with a cylindrical elliptical reflector 82, as illustrated in FIGS. 5 and 6. The cylindrical elliptical reflector provides a line of reflected light, rather than a point, at the second focal point. A cylindrical lens 84 is placed at the second focal point in order to convert the line to a point. The lens 84 and reflector 82 have different focal points, and the offset of the lens from the reflector is arranged to make the two focal points coincide near the optical guide input at output port 14. The optics used are suitably fused silica, to ensure transmission of the UVB radiation. The remainder of the optics will be the same as in FIGS. 1 and 2.

Figure 7:
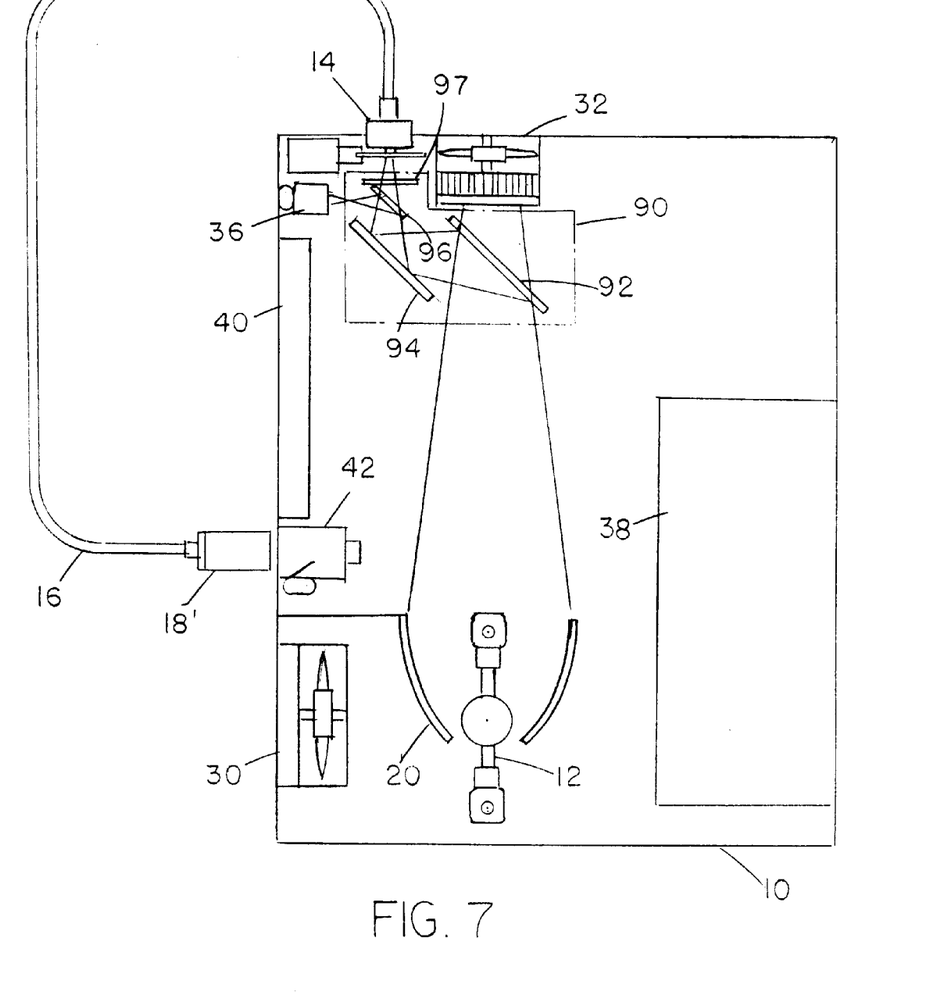
FIG. 7 is a block diagram of a targeted UVB phototherapy apparatus according to another embodiment of the invention.

In the embodiments of FIGS. 1 and 2, the desired wavelength range of 300 to 320 nm. (UVB) or 330 to 380 nm (UVA) is isolated using UVB reflective dichroic mirrors, or a combination of UVB and UVA reflective dichroic mirrors. FIG. 7 illustrates another embodiment of the invention in which UVB radiation, or UVA and UVB radiation, is isolated in a different way, replacing the mirrors of FIG. 1 with an alternative isolation assembly 90. The apparatus of FIG. 7 is otherwise identical to that of FIG. 1, and like reference numerals have been used as appropriate. The UV isolation assembly 90 of FIG. 7 comprises a combination of a broadband dichroic UV mirror 92 and a pivotally mounted diffraction grating 94. The UV mirror 92 will reflect a large portion of the UV light emitted from lamp 12 towards the diffraction grating 94. The diffraction grating 94 faces a beam splitter 96, suitably a 5% quartz beam splitter. Part of the beam emitted by beam splitter 96 is directed to sensor 36 for continuous monitoring the lamp output, while the remainder is directed towards the output port 14. An aperture 97 is positioned between the diffraction grating and output port for determining the portion of the spectrum transmitted to port 14.

The grating 94 in one example is a Monk-Gillieson configuration plane diffraction grating, used for situations where a converging beam strikes a plane diffraction grating.

The converging beam first strikes the broadband, dichroic UV mirror, eliminating the visible and IR wavelengths. This strongly reduces the radiant flux on the diffraction grating, prolonging its useful life, and allows the wasted energy to be concentrated on the heat sink 32. The grating can be pivoted such that a predetermined part of the emitted spectrum is directed through aperture 97 to the output port 14, such as the UVB 300–320 nm. light, or the UVA 330 to 380 nm. light. A suitable control will be provided on the housing control panel to allow the operator to pivot the grating to the appropriate position. The grating may also be mounted on a base that is adjustable to allow for the aperture 97 to be fixed in front of the optical guide. Operation of the apparatus of FIG. 7 is otherwise identical to that of the previous embodiments.

The phototherapy apparatus of this invention provides an efficient and inexpensive means for selective targeting of UV radiation to dermatoses, and is particularly useful for treating psoriasis and vitiligo. The apparatus can be used by the patient at home, rather than only at a doctor's office or hospital as in the case of more expensive and sensitive laser-based systems. The apparatus is designed to deliver radiation primarily in the 300 to 320 nm. UVB range from an inexpensive source comprising a medium pressure mercury, mercury xenon, or doped mercury arc lamp, and in one embodiment has an extra port for optional delivery of radiation primarily in the UVA range. Since radiation is delivered only to the plaque area of the skin, the dosage can be higher than for booth treatments where healthy skin is also exposed, potentially reducing the number of treatments needed. The dosage confined to a plaque area may be up to six times the estimated MED for a patient.

The efficacy of the radiation delivered by this apparatus is increased or maximized by maintaining the majority of the radiation delivered in the range of highly therapeutic radiation, e.g. 90% of the radiation delivered is in the 300–320 nm. range where UVB radiation is used, and by eliminating the non-therapeutic, potentially harmful wavelengths found in conventional UVB fluorescent bulbs.

In the first embodiment of the invention described above, the desired wavelength range of UVB radiation is obtained by means of multiple UVB cold mirrors, rather than bandpass or absorption filters which have high transmission inefficiency and therefore require use of a very high power source. This arrangement results in loss of only about 10% of the radiation within the desired range, and can use a much lower power UV source. The handpiece coupled to the flexible light guide provides a stable and readily maneuverable means for accurate, targeted UV radiation delivery with little or no leakage of UV radiation outside the area being targeted.

Although some exemplary embodiments of the invention have been described above by way of example only, it will be understood by those skilled in the field that modifications may be made to the disclosed embodiments without departing from the scope of the invention, which is defined by the appended claims.

I claim:

1. A UV phototherapy apparatus, comprising:
   a base unit having an output port for delivery of UVB radiation within a predetermined range;
   a flexible elongate optical guide having an input end connected to the output port of the base unit and an output end; and
   a handpiece having an input end connected to the output end of the optical guide, and an exit aperture of predetermined, non-circular shape for delivering radiation to a target area of a patient;
   the base unit including a UVB lamp for emitting UVB radiation in a predetermined range, a focusing device for focusing the radiation from the UVB lamp along an optical path onto the input end of the optical guide, and a beam isolating assembly in the optical path for isolating UVB radiation in the predetermined range from the lamp output, whereby at least 90% of the radiation directed into the optical guide is in the predetermined range.

2. The apparatus as claimed in claim 1, wherein the predetermined range is from 300 nm. to 320 nm.

3. The apparatus as claimed in claim 1, wherein the lamp emits UVB radiation in at least two peak wavelengths, and the output from the handpiece is primarily a mixture of the two radiation peak wavelengths.

4. The apparatus as claimed in claim 3, wherein the output radiation is a mixture of UVB radiation at around 302 nm. and 312 nm.

5. The apparatus as claimed in claim 3, wherein the output radiation is a mixture of UVB radiation at three different wavelengths of approximately 302 nm., approximately 312 nm., and approximately 318 nm.

6. The apparatus as claimed in claim 1, wherein the beam isolating assembly comprises at least one UVB reflective dichroic mirror for reflecting radiation in the predetermined range along the optical path while transmitting radiation outside the range.

7. The apparatus as claimed in claim 6, wherein the beam isolating assembly comprises two UVB reflective dichroic mirrors arranged in series along the optical path.

8. The apparatus as claimed in claim 7, wherein the beam isolating assembly further comprises an edge filter positioned in the beam path after the second dichroic mirror.

9. The apparatus as claimed in claim 1, wherein the beam isolating assembly comprises a grating.

10. The apparatus as claimed in claim 9, wherein the beam isolating assembly further comprises a broadband dichroic UV mirror positioned to direct primarily UV radiation from the lamp onto the grating.

11. The apparatus as claimed in claim 1, wherein the UV lamp is an arc lamp and the focusing device is a reflector.

12. The apparatus as claimed in claim 11, wherein the reflector is a UV reflective, dichroic coated glass.

13. The apparatus as claimed in claim 11, wherein the UV lamp is a short arc lamp and the reflector comprises a symmetric elliptical reflector.

14. The apparatus as claimed in claim 11, wherein the UV lamp is a medium arc lamp, the reflector is a cylindrical elliptical reflector, and a cylindrical lens is located at a focus of the reflector for focusing the light output of the reflector at the output port.

15. The apparatus as claimed in claim 1, wherein the base unit has a second output port for UVA radiation and the beam isolating assembly includes a first isolating portion for isolating UVB radiation in the predetermined range and directing the isolated UVB radiation to the UVB output port, and a second isolating portion for isolating UVA radiation in a predetermined range and directing the isolated UVA radiation to the second output port.

16. The apparatus as claimed in claim 15, wherein the first isolating portion comprises at least one UVB reflective dichroic mirror in the optical path from the lamp to the UVB output port for reflecting UVB radiation along the optical path and transmitting substantially all non-UVB radiation outside the UVB range along a second optical path, and the second isolating portion comprises at least one UVA reflective dichroic mirror positioned in the second optical path for reflecting radiation in a predetermined UVA range to the second output port and transmitting radiation outside the UVA range.

17. The apparatus as claimed in claim 16, wherein the first isolating portion comprises two UVB reflective dichroic mirrors arranged in series, and the second isolating portion comprises two UVA reflective dichroic mirrors arranged in series.

18. The apparatus as claimed in claim 15, wherein the optical guide is selectively releasably securable to the UVB output port or the second, UVA output port.

19. The apparatus as claimed in claim 15, including a second optical guide having a first end secured to the second output port and a second end, and a second handpiece secured to the second end of the optical guide for applying targeted UVA radiation to a selected area of skin.

20. The apparatus as claimed in claim 1, wherein the lamp is a short arc mercury lamp.

21. The apparatus as claimed in claim 1, wherein the lamp is a short arc lamp selected from the group consisting of mercury, xenon mercury, and doped mercury short arc lamps.

22. The apparatus as claimed in claim 1, wherein the lamp is a medium arc lamp selected from the group consisting of doped metal halide and tubular mercury arc lamps.

23. The apparatus as claimed in claim 1, wherein the optical guide is selected from the group consisting of a UV transmissive liquid light guide, a fused silica fiberoptic guide, and a fused silica fiberoptic bundle.

24. The apparatus as claimed in claim 1, further comprising a beam shutter mounted in the path from the lamp to the output port and movable between an extended, closed position blocking transmission of radiation to the output port, and a retracted, open position allowing transmission of radiation to the output port, and a control unit for controlling operation of the shutter according to a programmed treatment cycle.

25. The apparatus as claimed in claim 1, wherein the handpiece comprises a hollow tube of rectangular cross-section and of a UV blocking material, the tube having a first end wall having an input port to which the output end of the optical guide is connected, and a second end having an exit aperture of rectangular cross-section for applying a beam of corresponding cross-section to an underlying skin area.

26. The apparatus as claimed in claim 25, wherein the tube has an internal chamber between the input port and exit aperture for shaping the beam from a circular shape to a rectangular shape.

27. The apparatus as claimed in claim 25, wherein a fused silica rod of rectangular cross-section is secured in the second end of the handpiece tube, the rod having an outer end face defining said exit aperture.

28. The apparatus as claimed in claim 25, further comprising a rectangular tip secured to the second end of the tube and protruding from the tube beyond the exit aperture, the tip being of a UV blocking material.

29. The apparatus as claimed in claim 28, wherein the tip is releasably secured to the tube.

30. The apparatus as claimed in claim 28, wherein the tip is of light transmissive, UV blocking material.

31. The apparatus as claimed in claim 28, wherein the tip has an outer peripheral end edge, and at least one porous pad is secured to extend around at least part of the peripheral end edge and contact a patient's skin during treatment, the porous pad containing a marking material for marking the skin of a patient to indicate an area which has been treated.

32. A method of treating lesional tissue with targeted UVB radiation, comprising the steps of:
   directing radiation from a UVB lamp source along an optical path;
   isolating radiation in a predetermined UVB range from the radiation spectrum emitted by the lamp source and directing the isolated UVB radiation into one end of a maneuverable, elongate optical guide;
   connecting the other end of the optical guide to a handpiece having an exit aperture of predetermined, non-circular shape for directing the isolated radiation onto a predetermined target area of tissue to be treated;
   optically shaping the beam in the handpiece from a round cross-section to a straight edged cross-section beam emitted from the exit aperture;
   applying UVB radiation from the exite aperture to the target area for a predetermined time period;
   moving the handpiece to an adjacent area and applying UVB radiation from the exit aperture to the adjacent area for the same time period; and
   repeating the procedure until the entire lesional area has been treated.

* * * * *